United States Patent
Levitz et al.

(10) Patent No.: US 10,440,991 B2
(45) Date of Patent: Oct. 15, 2019

(54) RESERVOIR FILLING SYSTEM FOR AN ELECTRONIC VAPING DEVICE

(71) Applicant: Altria Client Services LLC, Richmond, VA (US)

(72) Inventors: Robert Levitz, North Miami Beach, FL (US); Arie Holtz, Jerusalem (IL)

(73) Assignee: Altria Client Services LLC, Richmond, VA (US)

( * ) Notice: Subject to any disclaimer, the term of this patent is extended or adjusted under 35 U.S.C. 154(b) by 905 days.

(21) Appl. No.: 14/933,551

(22) Filed: Nov. 5, 2015

(65) Prior Publication Data

US 2016/0120227 A1    May 5, 2016

Related U.S. Application Data

(60) Provisional application No. 62/075,432, filed on Nov. 5, 2014.

(51) Int. Cl.

| | |
|---|---|
| *A24F 47/00* | (2006.01) |
| *B65B 3/06* | (2006.01) |
| *H05B 3/06* | (2006.01) |
| *F16K 5/06* | (2006.01) |

(Continued)

(52) U.S. Cl.
CPC .......... *A24F 47/008* (2013.01); *F16K 15/183* (2013.01); *H05B 3/06* (2013.01); *H05B 3/44* (2013.01); *A61M 2209/045* (2013.01); *H05B 2203/014* (2013.01); *H05B 2203/021* (2013.01); *H05B 2203/022* (2013.01)

(58) Field of Classification Search
None
See application file for complete search history.

(56) References Cited

U.S. PATENT DOCUMENTS

| | | |
|---|---|---|
| 1,302,933 A | 5/1919 | Langton |
| 3,146,808 A | 9/1964 | Zellweger |
| 3,174,519 A | 3/1965 | Pizzurro et al. |

(Continued)

FOREIGN PATENT DOCUMENTS

| | | |
|---|---|---|
| CA | 2844684 A1 | 3/2013 |
| CN | 103 760 570 A | 4/2014 |

OTHER PUBLICATIONS

International Preliminary Report for corresponding International application No. PCT/US2015/059254 dated May 9, 2017.

(Continued)

*Primary Examiner* — Joseph M Pelham
(74) *Attorney, Agent, or Firm* — Harness, Dickey & Pierce, P.L.C.

(57) ABSTRACT

A reservoir refill system for an electronic vaping device includes a refill container and a reservoir. The refill container contains a pre-vapor formulation. The refill container includes a body, an opening in the body, and a first interlocking ring including at least one groove or at least one protrusion therein. The reservoir is configured to contain a pre-vapor formulation and includes a reservoir body, an opening in the reservoir body, and a second interlocking ring including at least one groove or at least one protrusion therein at an opening of the reservoir. The first interlocking ring is configured to mate with the second interlocking ring so as to release the pre-vapor formulation from the refill container to the reservoir.

22 Claims, 10 Drawing Sheets

(51) Int. Cl.
*H05B 3/44* (2006.01)
*F16K 15/18* (2006.01)

(56) References Cited

U.S. PATENT DOCUMENTS

| | | | |
|---|---|---|---|
| 3,217,762 | A | 11/1965 | Burchett |
| 7,507,491 | B2 | 3/2009 | Finkelshtain et al. |
| 8,757,169 | B2 | 6/2014 | Gysland |
| 8,955,522 | B1 | 2/2015 | Bowen et al. |
| 9,247,773 | B2 * | 2/2016 | Memari ................. A24F 15/12 |
| 10,015,995 | B2 * | 7/2018 | Memari ................. A24F 15/12 |
| 10,015,996 | B2 * | 7/2018 | Memari ................. A24F 15/12 |
| 10,070,662 | B2 * | 9/2018 | Gorilovsky .......... A24B 15/167 |
| 2010/0126505 | A1 | 5/2010 | Rinker |
| 2010/0242975 | A1 | 9/2010 | Hearn |
| 2011/0315152 | A1 | 12/2011 | Hearn et al. |
| 2012/0167906 | A1 | 7/2012 | Gysland |
| 2012/0273589 | A1 | 11/2012 | Hon |
| 2013/0192615 | A1 * | 8/2013 | Tucker ................. H01C 17/00 131/328 |
| 2014/0076310 | A1 | 3/2014 | Newton |
| 2014/0283946 | A1 | 9/2014 | Kribs |
| 2015/0245654 | A1 * | 9/2015 | Memari ................. A24F 15/12 141/2 |
| 2015/0282530 | A1 * | 10/2015 | Johnson ................ A24F 47/008 392/387 |
| 2016/0120226 | A1 * | 5/2016 | Rado .................... A24F 47/008 131/329 |
| 2016/0366946 | A1 * | 12/2016 | Murison ................ A24F 15/12 |
| 2017/0020197 | A1 * | 1/2017 | Cameron ............. A24F 47/008 |
| 2017/0043999 | A1 * | 2/2017 | Murison ............... H05B 1/0227 |
| 2017/0045150 | A1 * | 2/2017 | Marsh ................... A24F 15/18 |
| 2017/0045994 | A1 * | 2/2017 | Murison ................ A24F 15/18 |
| 2017/0048927 | A1 * | 2/2017 | Murison ................ A24F 15/18 |
| 2017/0048930 | A1 * | 2/2017 | Marsh ................... A24F 15/18 |
| 2018/0084830 | A1 * | 3/2018 | Xu ....................... A24F 47/008 |

OTHER PUBLICATIONS

International Search Report PCT/ISA/210 and Written Opinion of the INternational Searching Authority PCT/ISA/237 for International Application No. PCT/US2015/059254 dated Mar. 15, 2016.

* cited by examiner

RESERVOIR FILLING SYSTEM FOR AN ELECTRONIC VAPING DEVICE

PRIORITY STATEMENT

This application is a non-provisional application that claims priority to U.S. provisional app. No. 62/075,432, filed on Nov. 5, 2014, the entire contents of which is incorporated by reference in its entirety.

BACKGROUND

Field

The present disclosure relates to an electronic vaping device configured to deliver a pre-vapor formulation from a reservoir to a heater. The reservoir may be a container, such as a bottle or a tank that has a neck. The reservoir may be refillable.

Description of Related Art

An electronic vaping device includes a heater element, which vaporizes a pre-vapor formulation to produce a vapor. The heater element may include a resistive heater coil, with a wick extending there through.

SUMMARY

At least one example embodiment relates to a refill container.

In at least one example embodiment, a refill container includes a body containing a formulation, an opening in the body, and a first interlocking ring at the opening of the body. The first interlocking ring includes at least one of a groove and a protrusion therein. The interlocking ring is configured to mate with a second interlocking ring attached to a reservoir configured to hold the formulation.

In at least one example embodiment, the refill container further includes a ball valve in a neck of the opening and a crown adjacent the spring loaded ball. The ball valve includes a spring loaded ball, and the crown is configured to shield the spring loaded ball from being accessed. The refill container may further include a cap integrally formed with the first interlocking ring.

At least one example embodiment relates to a cartridge of an electronic vaping device including a reservoir.

In at least one example embodiment, a cartridge of an electronic vaping device includes a reservoir. The reservoir is configured to contain a pre-vapor formulation. The reservoir is refillable. The reservoir includes an opening and a first interlocking ring at the opening. The first interlocking ring includes at least one of a groove and a protrusion. The first interlocking ring is configured to connect to a second interlocking ring attached to a refill container.

In at least one example embodiment, the first interlocking ring includes at least one of a plurality of grooves and a plurality of protrusions spaced about a circumference of the first interlocking ring. The opening in the reservoir may further include a valve. The valve includes a spring loaded disk and a gasket. The reservoir may also include a chimney support configured to maintain the spring loaded disk in place until the first interlocking ring is connected to a second interlocking ring.

At least one example embodiment relates to an electronic vaping device.

In at least one example embodiment, an electronic vaping device includes a housing extending in a longitudinal direction, a reservoir configured to contain a pre-vapor formulation, and a heater in fluid communication with the reservoir. The reservoir is refillable. The reservoir includes an opening and a first interlocking ring at the opening. The first interlocking ring includes at least one of a groove and a protrusion. The first interlocking ring is configured to connect to a second interlocking ring attached to a refill container.

In at least one example embodiment, the first interlocking ring includes at least one of a plurality of grooves and a plurality of protrusions spaced about a circumference of the first interlocking ring. The opening in the reservoir may further include a valve. The valve includes a spring loaded disk and a gasket.

In at least one example embodiment, the electronic vaping device may also include a chimney support configured to maintain the spring loaded disk in place until the first interlocking ring is connected to a second interlocking ring.

At least one example embodiment relates to a reservoir refill system.

In at least one example embodiment, a reservoir refill system includes a refill container containing a pre-vapor formulation and a reservoir configured to contain a pre-vapor formulation. The refill container includes a container body, an opening in the container body, and a first interlocking ring including at least one of a groove and a protrusion therein positioned at the opening in the container body. The reservoir includes a reservoir body configured to contain the pre-vapor formulation, an opening in the reservoir body, and a second interlocking ring including at least one of a groove and a protrusion therein. The second interlocking ring is positioned at the opening in the reservoir body. The first interlocking ring is configured to connect to the second interlocking ring.

In at least one example embodiment, at least one of the first interlocking ring and the second interlocking ring is colored. The first interlocking ring and the second interlocking ring may be the same color. At least one of the first interlocking ring and the second interlocking ring may include at least one of a plurality of grooves and a plurality of protrusions spaced about a circumference thereof. At least one of the first interlocking ring and the second interlocking ring may be formed of plastic.

In at least one example embodiment, the opening in the reservoir may further includes a valve. The valve includes a spring loaded disk and a gasket.

In at least one example embodiment, the reservoir further includes a chimney support configured to maintain the spring loaded disk in place until the first interlocking ring is connected to a second interlocking ring.

In at least one example embodiment, the refill container may further include a ball valve in a neck of the opening. The ball valve includes a spring loaded ball and a crown adjacent the spring loaded ball. The crown is configured to shield the spring loaded ball from being accessed.

In at least one example embodiment, at least one of the first interlocking ring and the second interlocking ring is impregnated with at least one of a flavorant and a chemesthesis agent having one or more of a spicy, bitter, and sour taste. At least one of the first interlocking ring and the second interlocking ring may include a coating comprising at least one of a flavorant and a chemesthesis agent having one or more of a spicy, bitter, and sour taste.

In at least one example embodiment, a cap is integrally formed with the first interlocking ring.

At least one example embodiment relates to a reservoir refill system.

In at least one example embodiment, a reservoir refill system includes a refill container containing a pre-vapor formulation and a reservoir configured to contain a pre-vapor formulation. The refill container includes a container body, an opening in the container body, and a perforated disk having one or more holes therein. The reservoir includes a reservoir body configured to contain the pre-vapor formulation, an opening in the reservoir body, and a crown including one or more teeth thereon. The teeth are sized and configured to be received in the one or more holes in the perforated disk.

In at least one example embodiment, the reservoir refill system may also include a first interlocking ring including one or more of at least one groove and at least one protrusion therein at an opening in one of the container body and the reservoir body. The reservoir refill system may also include a second interlocking ring including one or more of at least one groove and at least one protrusion therein at an opening of one of the container body and the reservoir body.

In at least one example embodiment, at least one of the first interlocking ring and the second interlocking ring is impregnated with at least one of a flavorant and a chemesthesis agent having one or more of a spicy, bitter, and sour taste. At least one of the first interlocking ring and the second interlocking ring may include a coating comprising at least one of a flavorant and a chemesthesis agent having one or more of a spicy, bitter, and sour taste.

At least one example embodiment relates to a method of refilling a reservoir.

In at least one example embodiment, a method of refilling a reservoir of an electronic vaping device includes inserting at least one protrusion of a first interlocking ring into at least one groove of a second interlocking ring so as to engage a spring loaded ball of a refill container and a spring loaded disk of a reservoir, and releasing a formulation from the refill container to the reservoir.

At least one example embodiment relates to a cartridge of an electronic vaping device.

In at least one example embodiment, a cartridge includes a housing extending in a longitudinal direction and a chimney extending in the longitudinal direction. The chimney is in the housing. The chimney includes at least one protrusion along a length of the chimney, and at least one stop along the length of the chimney. The cartridge also includes a reservoir configured to contain a pre-vapor formulation. The reservoir is refillable. The reservoir is between the housing and the chimney. The cartridge also includes a valve circumscribing the chimney. The valve includes a first ring abutting the at least one stop, a second ring abutting the at least one protrusion, and at least one pillar connecting the first ring and the second ring, the valve being formed of a flexible material.

In at least one example embodiment, the at least one pillar is generally convex and the second ring has a larger diameter than the first ring. The flexible material may be rubber.

In at least one example embodiment, the at least one pillar is generally concave and the first ring has a larger diameter than the second ring.

At least one example embodiment relates to a reservoir refill system.

In at least one example embodiment, a reservoir refill system includes a refill container containing a pre-vapor formulation and a cartridge configured to hold the pre-vapor formulation. The refill container includes a container body, an opening in the container body, and a ball valve assembly positioned at the opening. The ball valve assembly includes a ball valve portion, a shoulder portion extending from the ball valve portion, the shoulder portion including one or more openings extending therethrough, and a gasket portion integrally formed with the ball valve. The gasket portion is connected to the ball valve by the shoulder portion. The cartridge is configured to mate with the refill container. The cartridge includes a housing extending in a longitudinal direction and a chimney extending in the longitudinal direction. The chimney is in the housing. The chimney includes at least one protrusion along a length of the chimney, and at least one stop along the length of the chimney. The cartridge also includes a reservoir that configured to contain a pre-vapor formulation. The reservoir is refillable, and the reservoir is between the housing and the chimney. A valve circumscribes the chimney. The valve includes a first ring abutting the at least one stop, a second ring abutting the at least one protrusion, and at least one pillar connecting the first ring and the second ring. The valve is formed of a flexible material.

In at least one example embodiment, a refill container containing a pre-vapor formulation includes a container body, an opening in the container body, and a ball valve assembly positioned at the opening. The ball valve assembly includes a ball valve portion, a shoulder portion extending from the ball valve portion, the shoulder portion including one or more openings extending therethrough, and a gasket portion integrally formed with the ball valve, the gasket portion connected to the ball valve by the shoulder portion.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
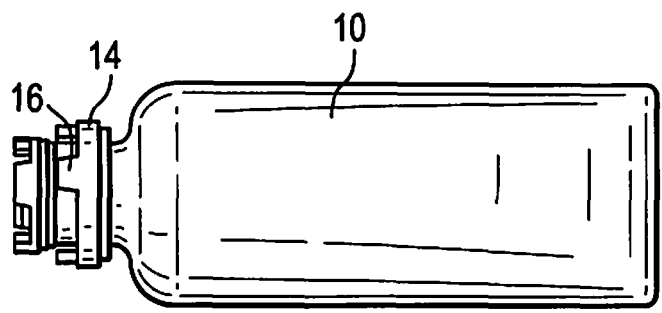
FIG. 1 is a side view of a refill bottle including a male interlocking ring for mating with a female interlocking ring according to at least one example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

At least one example embodiment is related to a refill container that contains a pre-vapor formulation. Pre-vapor formulation refills may be provided in containers, such as tubes and/or bottles that are sold separately or with an electronic vaping device. The tubes may be compressible and may reduce in size after emptying, while bottles may be compressible or rigid, but maintain shape when emptied. The refills may be contained in any suitable container having any suitable size and shape.

In at least one example embodiment, the pre-vapor formulation may be a material or combination of materials that may be transformed into a vapor. For example, the pre-vapor formulation may be a liquid, solid and/or gel formulation including, but not limited to, water, beads, solvents, active ingredients, ethanol, plant extracts, natural or artificial flavors, and/or vapor formers, such as glycerin and propylene glycol.

FIG. 1 is a side view of a refill bottle including a male interlocking ring for mating with a female interlocking ring of a reservoir and/or a cartridge according to at least one example embodiment.

In at least one example embodiment, as shown in FIG. 1, a refill bottle (or container) 10 may include a male interlocking ring 14 having at least one protrusion 16 (e.g., at least 2, at least 3, at least 4, at least 5, etc.) thereon. In at least one example embodiment, the at least one protrusion 16 of the male interlocking ring 14 is sized and configured to be received in a groove 22 of a female interlocking ring 20 as described below with respect to FIG. 6.

Figure 2:
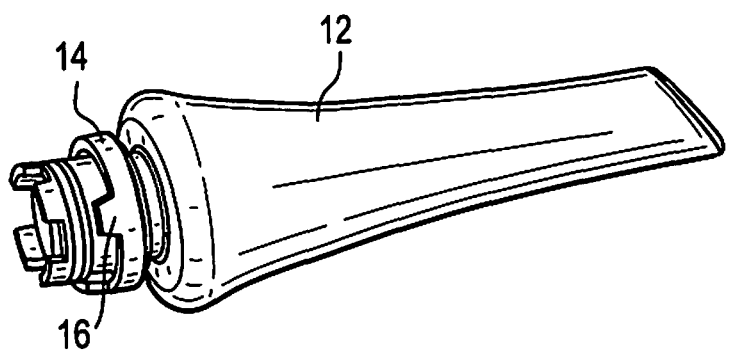
FIG. 2 is a side view of a refill tube including a male interlocking ring for mating with a female interlocking ring according to at least one example embodiment.

FIG. 2 is a side view of a refill tube including a male interlocking ring configured to mate with the female interlocking ring of a reservoir according to at least one example embodiment.

In at least one example embodiment, as shown in FIG. 2, instead of the refill bottle 10 of FIG. 1, the pre-vapor formulation refill may be stored in a refill tube (or container) 12 including the male interlocking ring 14. The refill tube 12 may have a different shape and/or size than the refill bottle 10, and may be formed of a flexible material, such that the tube 12 may be squeezed to aid in releasing the pre-vapor formulation when the tube 12 is mated with a reservoir.

Figure 3:
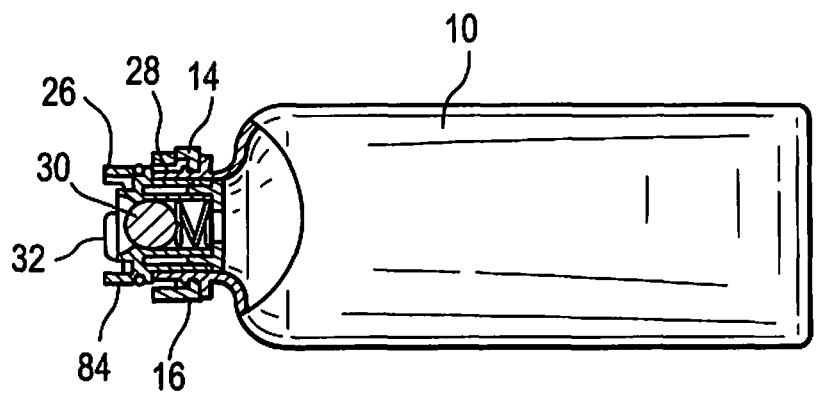
FIG. 3 is an enlarged, side, cross-sectional view of a refill bottle including a male interlocking ring for mating with a female interlocking ring according to at least one example embodiment.

FIG. 3 is a side, cross-sectional view of a male interlocking ring for mating with a female interlocking ring of a reservoir according to at least one example embodiment.

Figure 6:
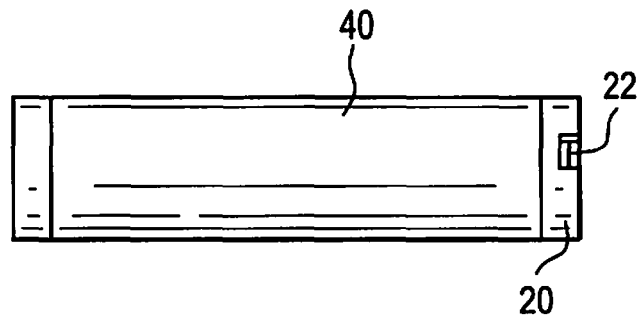
FIG. 6 is a side view of a cartridge including a female interlocking ring according to at least one example embodiment.

In at least one example embodiment, as shown in FIG. 3, the refill bottle 10 or tube 12 (not shown) may include a ball valve 26 in a container neck 28 at an outlet of the refill bottle 10 or tube 12. The ball valve 26 substantially prevents and/or reduces the release of pre-vapor formulation when the bottle 10 or tube 12 is overturned or squeezed. In at least one example embodiment, the pre-vapor formulation is only released when a spring-loaded ball 30 of the ball valve 26 in the container neck 28 of the bottle 10 or tube 22 (or container) is pushed in. A crown 32 adjacent the spring-loaded ball 30 may substantially prevent a person from accessing the spring-loaded ball 30 and pushing the spring-loaded ball 30 in so as to prevent and/or reduce release of the pre-vapor formulation unless the refill bottle 10 is mated with a reservoir or cartridge to be refilled. In at least one example embodiment, as shown in FIG. 3, the spring-loaded ball 30 is pushed in when the male interlocking ring 14 of the refill bottle 10 or tube 12 is mated with a female interlocking ring 20 as shown in FIG. 6 and discussed below.

In at least one example embodiment, as shown in FIG. 3, the male interlocking ring 14 includes at least one protrusion 16 that are inserted in perforations in a portion of a female interlocking ring as described below with reference to FIGS. 8 and 9. In addition, the teeth 84 on a crown 26 are sized and configured to mate with perforations 64 of a perforated disk 62 (shown in FIG. 8).

Figure 4:
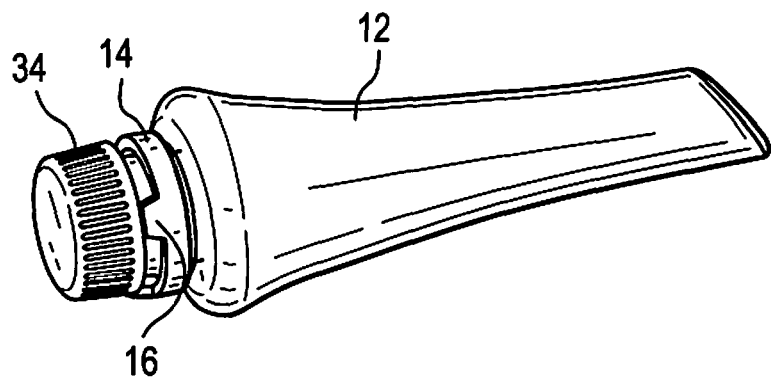
FIG. 4 is an enlarged, side view of a capped refill tube including a male interlocking ring for mating with a female interlocking ring of a reservoir according to at least one example embodiment.

FIG. 4 is an enlarged, side view of a capped refill tube including a male interlocking ring for mating with a female interlocking ring according to at least one example embodiment.

In at least one example embodiment, as shown in FIG. 4, the male interlocking ring 14 is generally the same as that of FIG. 3 except that the male interlocking ring 14 is designed and manufactured as an integral part of a sealing cap 34. When the cap 34 is removed, by twisting off or by other removal methods, the male interlocking ring 14 detaches (e.g., breaks off) from the cap 34 and remains on the container neck 28 of the refill bottle 10 or tube 12.

Figure 5:
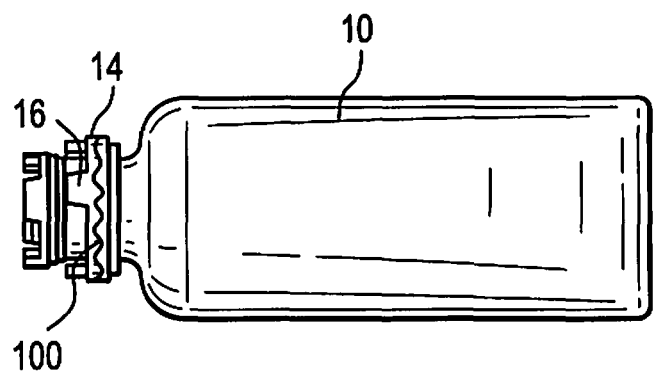
FIG. 5 is a side view of a refill bottle including a male interlocking ring including a coating applied at an opening of the refill bottle according to at least one example embodiment.

FIG. 5 is a side view of a refill bottle including a male interlocking ring including a coating applied at an opening of the refill bottle according to at least one example embodiment.

In at least one example embodiment, as shown in FIG. 5, the male interlocking ring 14 is generally the same as that of FIG. 3 except that the male interlocking ring 14 includes a coating 100 applied to an external surface of the male interlocking ring 14 and/or the male interlocking ring 14 is impregnated with a flavorant and/or chemesthesis agent. The flavorant and/or the chemesthesis agent may be any additive that is bitter, sour, and/or spicy, and which is generally unpleasing in taste. In at least one example embodiment, the flavorant and/or chemesthesis agent is food safe and non-toxic. For example, the flavorant and/or chemesthesis agent may include vinegar, cayenne pepper, other peppers, any bitter flavorant, and combinations of these. The inclusion of a coating 100 or impregnation with flavorants and/or chemesthesis agents as described herein may discourage and/or prevent a person from placing their mouth on the refill bottle 10 or tube 12 so as to assist in preventing and/or minimizing undesirable contact with the pre-vapor formulation.

FIG. 6 is a side view of a cartridge including a female interlocking ring according to at least one example embodiment.

In at least one example embodiment, as shown in FIG. 6, a cartridge (or first section) 40 of an electronic vaping device (not shown), contains a reservoir 18 (shown in FIG. 7) and includes a female interlocking ring 20 at an opening therein. The opening is in fluid communication with the reservoir 18. The female interlocking ring 20 may include at least one groove 22 (e.g., at least 2, at least 3, at least 4, at least 5, etc.) therein. The at least one groove 22 is sized and configured to receive the at least one protrusion 16 of the male interlocking ring 14 as described above.

Figure 7:
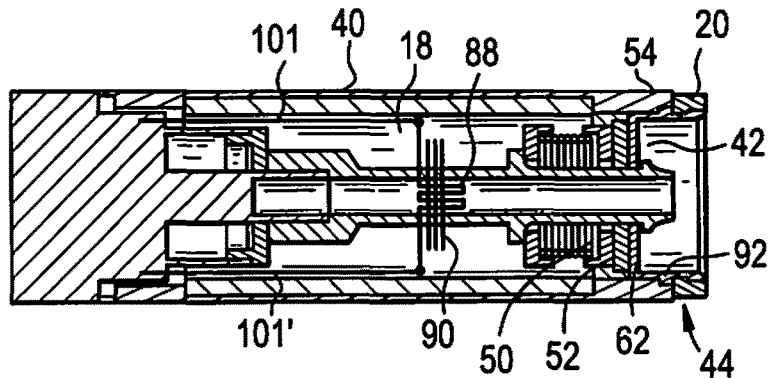
FIG. 7 is a cross-sectional view of the cartridge of FIG. 6 according to at least one example embodiment.

FIG. 7 is a cross-sectional view of a cartridge according to at least one example embodiment.

In at least one example embodiment, as shown in FIG. 7, the female interlocking ring 20 may surround an opening in the cartridge 40 and the opening is in fluid communication with the reservoir 18. The cartridge 40 also includes a valve 42 at a mouth-end 44 of the reservoir 18. The valve 42 substantially prevents and/or reduces the release of the pre-vapor formulation from the reservoir 18 when the cartridge 40 is overturned. The pre-vapor formulation may be received when a spring-loaded disk 50 including a gasket 52 in a neck 54 surrounding the opening is pushed in.

In at least one example embodiment, the spring-loaded disk 50 may not be seen or accessed when a mouth-end insert 44 or a mouthpiece 46 is connected to the cartridge 40 as discussed in detail below with respect to FIGS. 11-13. When the mouth-end insert 44 or mouthpiece 46 is disconnected from the cartridge 40, a chimney support 92 at the neck 19 substantially prevents a person from pushing the spring-loaded disk 50 in so as to substantially prevent and/or reduce release of the pre-vapor formulation when the reservoir 18 is not connected with the refill bottle 10 or tube 12. The reservoir 18 may also include a perforated disk 62.

In at least one example embodiment, a wick 90 extends into the reservoir 18. The wick delivers pre-vapor formulation from the reservoir 18 to a heater 88 discussed in detail below. Electrical leads 101, 101' extend from the heater 88 and complete an electrical connection with a battery or other power source as discussed below.

Figure 8:
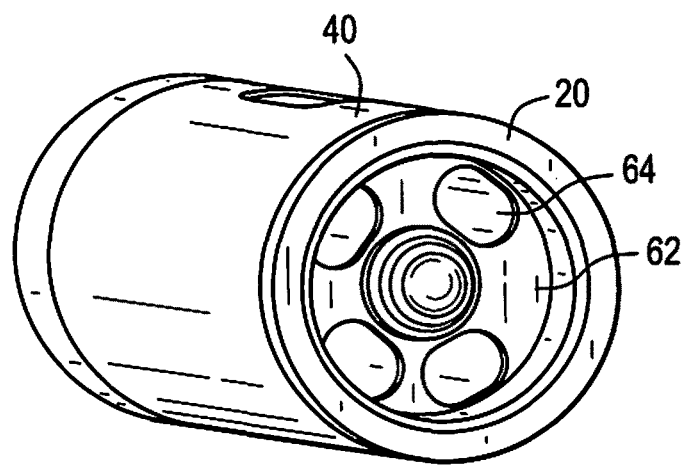
FIG. 8 is a perspective view of a cartridge according to at least one example embodiment.

FIG. 8 is an enlarged, perspective view of the cartridge 40 having the perforated disk 62 at an opening therein. As shown, the perforated disk 62 includes perforations 64 that are configured to receive the teeth 84 as associated with the crown 26 described with respect to FIG. 3 above. In at least one example embodiment, the perforations 64 are generally uniformly arranged on the face of the perforated disk 62. In other example embodiments, the perforations 64 may be irregularly spaced on the face of the perforated disk 62 such that the perforated disk 62 is asymmetrical. Thus, an asymmetrical perforated disk 62 may be formed to accept only specific refills.

Figure 9:
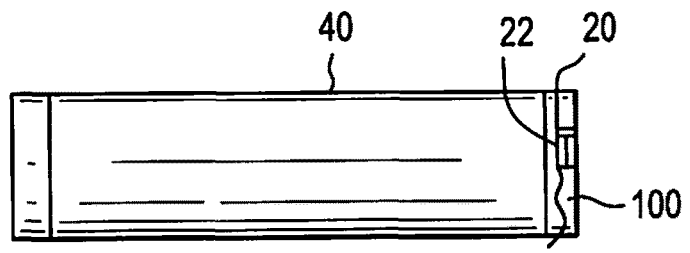
FIG. 9 is a side view of a cartridge including a female interlocking ring including a coating applied at an opening of the cartridge according to at least one example embodiment.

FIG. 9 is a side view of a cartridge and a female interlocking ring having a coating applied at an opening according to at least one example embodiment.

In at least one example embodiment, as shown in FIG. 9, a coating 100 may be applied to the female interlocking ring 20 and/or the female interlocking ring 20 may be impregnated with a flavorant and/or chemesthesis agent, which may be the same and/or different flavorant and/or chemesthesis agent applied to the male interlocking ring 14 as described above with respect to FIG. 5.

Figure 10:
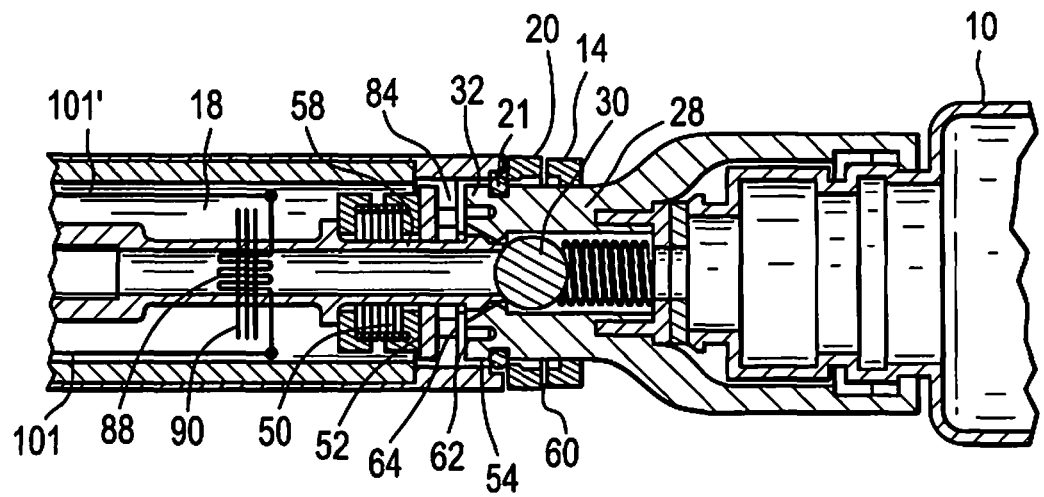
FIG. 10 is a side view of a cartridge mated with a refill bottle according to at least one example embodiment.

FIG. 10 is a side view of a cartridge mated with a refill bottle according to at least one example embodiment.

In at least one example embodiment, as shown in FIG. 10, to mate the cartridge 40 with the refill bottle 10 or tube 12, an adult vaper aligns the protrusions 16 on the male interlocking ring 14 with the grooves 22 on the female interlocking ring 20 and interlocks and/or friction or pressure fits the first section 40 and/or reservoir 18 with the refill bottle 10 or tube 12. As the male interlocking ring 14 of the refill bottle 10 or tube 12 is inserted into the female interlocking ring 20, an O-ring 56 may seal the opening of the reservoir 18 and the refill bottle 10 or tube 12 so as to substantially prevent and/or reduce leakage of the pre-vapor formulation during refill. Simultaneously, the crown 32 at the top of the male interlocking ring 14 of the refill bottle 10 or tube 12 presses against the spring-loaded disk 50 and gasket 52 to allow the pre-vapor formulation to enter the reservoir 18. In addition, the teeth 84 in the crown 32 of the refill bottle 10 or tube 12 are inserted through the perforations 64 in the perforated disk 62. The teeth 84 press the spring-loaded disk 50 downward and the spring-loaded ball 30 is pressed into contact the chimney (or inner tube) 58 that extends through the reservoir 18 so as to seal the chimney 38 from entry of pre-vapor formulation. Once the spring-loaded disk 50 is depressed and the spring-loaded ball 30 is pressed in and engaged with the chimney 58, the pre-vapor formulation is allowed to flow from the refill bottle 10 or tube 12 into the reservoir 18.

In at least one example embodiment, as shown in FIG. 10, when both the male interlocking ring 14 and the female interlocking ring 20 are completely mated together a stop 60 is formed. The stop 60 positions the refill bottle 10 or tube 12 relative to the reservoir 18 in a manner that assists and/or optimizes filling of the reservoir 18. Subsequent removal of the refill bottle 10 or tube 12 from the reservoir 18 causes sealing of the refill bottle 10 or tube 12 and the reservoir 18 so as to reduce and/or prevent leakage of the pre-vapor formulation.

In at least one example embodiment, the at least one groove 22 and the at least one protrusion 16 may have various different profiles so long as they are configured to mate together. In use, if the protrusions 22 and grooves 16 do not align, mating between a first section 40 and the refill bottle 10 may not occur and pre-vapor formulation may not be released, or at least not fully released, from the bottle 10 or tube 12. Moreover, the number of protrusions 16 and grooves 22 and the position of the protrusions 16 and grooves 22 on the male interlocking ring 14 and the female interlocking ring 20 may vary so long as the number of grooves 22 and positioning thereof is the same as the number and positioning of the protrusions 16. For example, the grooves 22 may be evenly spaced around a circumference of the female interlocking ring 20 or the grooves 22 may be unevenly spaced around the circumference of the female interlocking ring 20. Likewise, the protrusions 16 may be evenly spaced around a circumference of the male interlocking ring 14 or the protrusions 16 may be unevenly spaced around the circumference of the male interlocking ring 14.

In at least one example embodiment, the male interlocking ring 14 and the female interlocking ring 20 may be formed of a colored material, such as plastic. The color may indicate whether the male interlocking ring 14 and the female interlocking ring 20 are compatible for mating. Moreover, the color of the male interlocking ring 14 and the female interlocking ring 20 may be chosen to identify the flavor and/or aroma of the pre-vapor formulation included in the reservoir 18 and/or the refill bottle 10 or tube 12. Color coding of the rings 14, 20 may also prevent and/or reduce cross contamination as an adult vaper may easily identify the proper refill.

Figure 11:
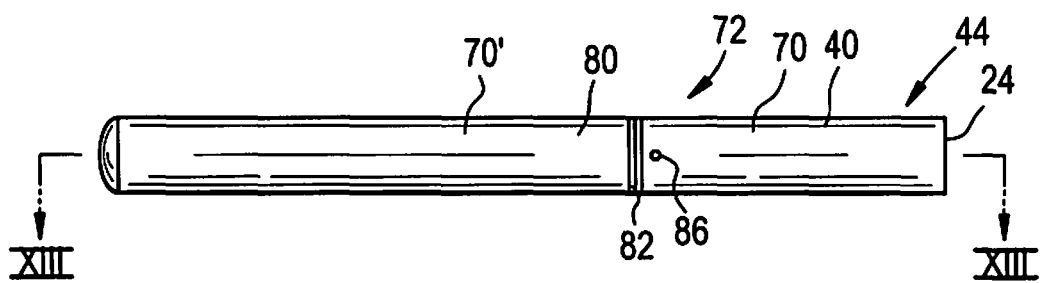
FIG. 11 is a top planar view of an electronic vaping device according to at least one example embodiment.

FIG. 11 is a top planar view of an electronic vaping device according to at least one example embodiment.

At least one example embodiment relates to an electronic vaping device 72 as shown in FIG. 11. The electronic vaping device 72 may include a first section or cartridge 40 and a second section 80. The first section 40 and the second section 80 may be connected by a connector 82 that may be a threaded connector or any other suitable connector. The electronic vaping device 72 includes an outer housing 70, 70' extending in a longitudinal direction. At least one air inlet 86 permits air to enter the electronic vaping device 72 during vaping. In some example embodiments, the air inlet 86 may be in the connector 82.

In at least one example embodiment, the housing 70, 70' of the electronic vaping device 72 may be formed of any suitable material or combination of materials. In at least one example embodiment, the housing 70, 70' is cylindrical and is formed at least partially of metal. Although the housing is described herein as cylindrical, other forms and shapes are contemplated.

Figure 12:
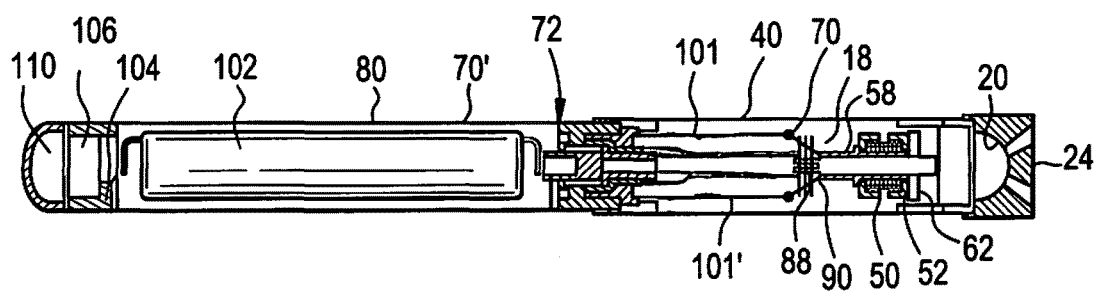
FIG. 12 is a cross-sectional view of the electronic vaping device of FIG. 12 along line XIII-XIII according to at least one example embodiment.

FIG. 12 is a cross-sectional view of an electronic vaping device according to at least one example embodiment.

In at least one example embodiment, as shown in FIG. 12, the reservoir 18 is housed in the cartridge 40. The reservoir 18 located in an outer annulus between an outer housing 70 and the chimney (inner tube) 58 as described in U.S. Patent Application Publication No. 2013/0192615 to Tucker et al., the entire content of which is incorporated herein by this reference thereto. In at least one example embodiment, the chimney 58 forms a central air passage, and the reservoir 18 at least partially surrounds the central air passage.

In at least one example embodiment, as shown in FIG. 12, the first section 40 may house the mouth-end insert 24, the heater 88, the wick 90 in fluid communication with the heater 88, and the reservoir 18. The second section 72 may house a power supply 102, a control circuit 104, and optionally a puff sensor 106.

In at least one example embodiment, the reservoir 18 may be refillable via an opening once the pre-vapor formulation is depleted.

In at least one example embodiment, the reservoir 18 stores the pre-vapor formulation and optionally a storage medium (not shown) configured to store the pre-vapor formulation therein. The wick 90 may extend into the reservoir 18 so as to deliver the pre-vapor formulation from the reservoir 18 to the heater 88, which heats the pre-vapor formulation to form a vapor.

In at least one example embodiment, the power supply 102 may include a battery arranged in the second section 80 of the electronic vaping device 72. The power supply 102 is configured to apply voltage across the heater 88. Thus, the heater 88 vaporizes a portion of the pre-vapor formulation according to a power cycle of a predetermined time period, such as a 0.5 to 10 second period.

In at least one example embodiment, the battery may be a Lithium-ion battery or one of its variants, for example a Lithium-ion polymer battery. In at least one example embodiment, the battery may be a Nickel-metal hydride battery, a Nickel cadmium battery, a Lithium-manganese battery, a Lithium-cobalt battery or a fuel cell. The electronic vaping device 72 may be vapable by an adult vaper until the energy in the power supply 102 is depleted. In at least one example embodiment, the power supply 102 may be rechargeable and may include a control circuit that allows the battery to be chargeable by an external charging device.

In at least one example embodiment, the control circuit 104 may be programmable and may include an application specific integrated circuit (ASIC). In at least one example embodiment, the control circuit 104 may include a microprocessor programmed to carry out functions such as heating.

In at least one example embodiment, the control circuit 104 may be arranged on a printed circuit board. The control circuit 104 may also include a heater activation light 110, such as a light-emitting diode (LED) that is configured to glow when the heater 88 is activated.

Figure 13:
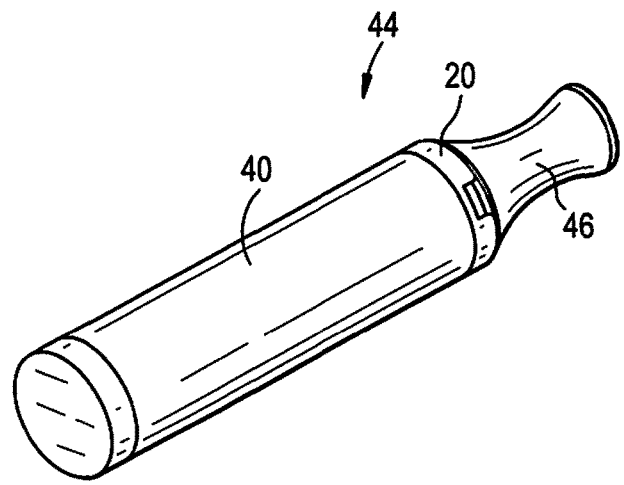
FIG. 13 is a perspective view of a cartridge including a mouthpiece according to at least one example embodiment.

FIG. 13 is a perspective view of a first section including a mouthpiece according to at least one example embodiment.

In at least one example embodiment, as shown in FIG. 13, the first section 40 houses the reservoir 18. A mouthpiece 46 may be positioned around a mouth-end 44 of the first section 40. The mouthpiece 46 may be removable so as to access and refill the reservoir 18. The first section 40 may be joined together with a separate battery section (shown in FIG. 13).

In some example embodiments, the female interlocking ring 20 may be associated with the refill bottle 10 or tube 12 and the male interlocking ring 14 may be associated with the first section 40 or the reservoir 18.

In at least one example embodiment, a refill system or kit can include a reservoir 18 or cartridge 40 including the reservoir 18 along with at least one refill bottle 10 and/or tube 12 including the male interlocking ring 14 and the female interlocking ring 20. The refill bottle 10 and/or tube 12 can include different pre-vapor formulations or the same pre-vapor formulations.

In at least one example embodiment, (not shown) the reservoir 18 may be a removable bottle, container, or other structure configured to hold the pre-vapor formulation rather than being integrally formed with a cartridge 40. The male and/or female locking ring 14, 20 may surround an opening in the reservoir 18 to facilitate refilling of the reservoir 18.

In at least one example embodiment, the tank refill system described herein allows for easy, leak-free and spill-free refilling of an electronic vaping device. Moreover, by color-coding the male and female interlocking rings, manufacturers may indicate which pre-vapor formulation and/or refills are compatible with specific electronic vaping devices. In addition, since at least one example embodiment of the refill may not be used without an electronic vaping device including a compatible interlocking ring, the refill and/or the device may not leak pre-vapor formulation, release pre-vapor formulation, or be accessed without first mating the interlocking rings. Thus, the tank refill system is a substantially child-proof system that substantially prevents and/or reduces exposure to the pre-vapor formulation.

In addition, it is contemplated that embodiments of the tank refill system described herein may be used in medical applications, such as for filling intravenous bags with medications without the use of a needle. Thus, the tank refill system may provide safer and easier refill of medical equipment and devices while also preventing and/or reducing refill of the wrong pre-vapor formulations.

In at least one example embodiment, the refill container (bottle 10 or tube 12) of the tank refill system may contain only liquid, suspension, solution, gas, or other flowable substances and/or formulations.

In at least one example embodiment, the male and female interlocking rings 14, 20 need not be included, but may be included as a secondary locking mechanism and/or to indicate whether the refill container will mate with the reservoir 18 and/or what flavor of pre-vapor formulation the refill container 10, 12 holds. Thus, the container and reservoir 18 may include only the valve 42 and the ball valve 26.

In at least one example embodiment, one or more additional safety mechanisms may be included in conjunction with the male and female interlocking rings 14, 20 and/or in conjunction with the perforated disk 62 and teeth 84 mechanism described above.

Figure 14:
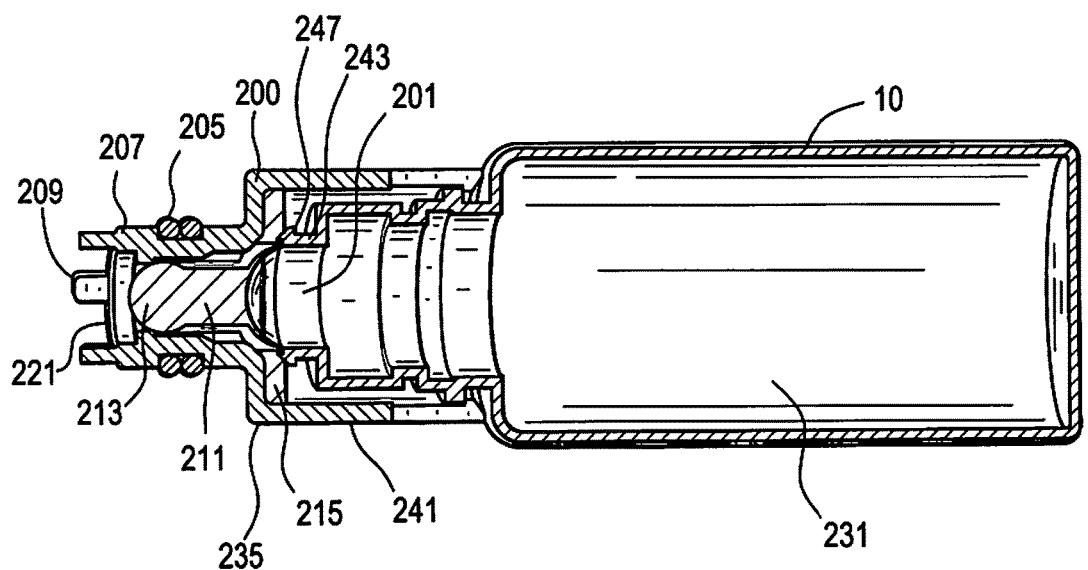
FIG. 14 is a cross-sectional view of a refill container according to at least one example embodiment.

FIG. 14 is a cross-sectional view of a refill container according to at least one example embodiment.

In at least one example embodiment, a refill container may include a refill interface 200 instead of the male and/or female interlocking ring as described above. As shown in FIG. 14, the refill bottle 10 or tube 12 may include the refill interface 200 positioned about an opening 201 in the bottle 10 or tube 12. The refill interface 200 includes a neck 207 that is configured to be inserted into a neck 450 (shown in FIG. 16) of a cartridge as described below. The neck 207 includes a shoulder portion 235 and at least one protrusion 209 extending from an end of the neck 207. At least one O-ring 205 circumscribes the neck 207. A base portion 241 of the refill interface 200 surrounds a side wall 243 that surrounds the opening 201 of the bottle 10. The side wall 243 may include a flange 247 against which the gasket portion 215 rests when a flexible ball valve assembly 211 rests in a closed position.

In at least one example embodiment, the flexible ball valve assembly 211 includes a ball valve 213 extending from a valve support 256. The flexible ball valve assembly 211 is positioned within the neck 207 of the refill interface 200, such that the flexible ball valve 213 blocks an opening 221 in the neck 207. The flexible ball valve 213 is integrally formed with a gasket portion 215 that is sized and configured to seal the opening 201 of the bottle 10 or tube 12. The gasket portion 215 of the flexible ball valve 213 has an outer surface that is generally cylindrical, such that the gasket portion 215 snugly fits within the neck 207. The gasket portion 215 extends from a valve shoulder portion 214 of the ball valve assembly 211. The shoulder portion 214 is connected to an end of the valve support 256 opposite from the ball valve 213. The shoulder portion 214 may be thinner than the valve support 256. When pressure is applied to the ball valve 213, the shoulder portion 214 flexes downwardly and bending of the valve support 256 is reduced and/or minimized.

In at least one example embodiment, the flexible ball valve assembly 211 is formed of a compressible and/or flexible material, such as rubber or plastic. The flexible ball valve assembly 211 is resilient such that the flexible ball valve 213 returns to an original state when pressure is not applied to the flexible ball valve 213.

Figure 15:
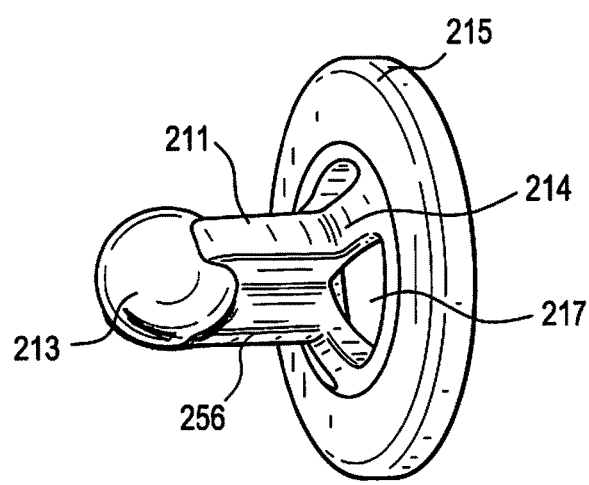
FIG. 15 is a perspective view of a ball valve of a refill container according to at least one example embodiment.

In at least one example embodiment, pre-vapor formulation is only released from the bottle 10 or container 12 when the flexible ball valve assembly 211 is pushed in and caused to flex. Once the flexible ball valve assembly 211 is pushed in, an opening between the ball valve 213 and the bottle neck occurs, such that the pre-vapor formulation may flow from a refill reservoir 231, through the openings 217 (shown in FIG. 15), through the neck 207, and into the reservoir 18 of the cartridge 40.

Figure 16:
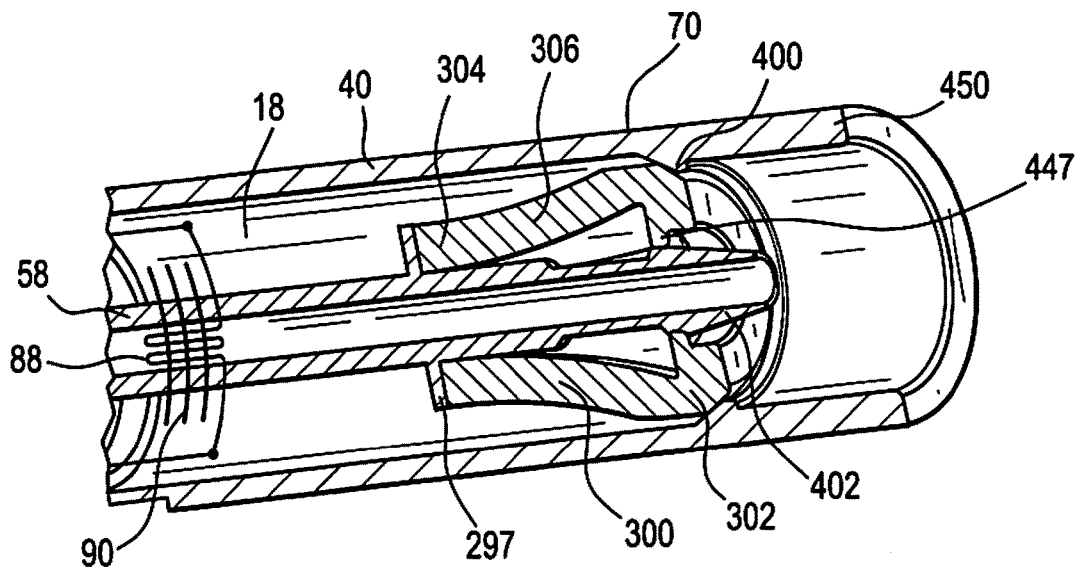
FIG. 16 is a cross-sectional, perspective view of a cartridge including a valve according to at least one example embodiment.

FIG. 16 is a cross-sectional, perspective view of a cartridge including a valve according to at least one example embodiment.

In at least one example embodiment, as shown in FIG. 16, the cartridge 40 may include a flexible valve 300 instead of the spring-loaded disk and female and/or male interlocking ring as described above. As shown in FIG. 16, the flexible valve 300 includes a first ring 302 connected to a second ring 304 by one or more pillars 206.

In at least one example embodiment, the housing 70 includes a neck 450 that surrounds the opening of the cartridge 40. The housing 70 may also include a stop 400 on an inner surface of the housing 70. The chimney 58 may include one or more chimney protrusions 297 around an outer surface of the chimney 58. The one or more chimney protrusions 297 may include a ring that circumscribes the chimney 58 or a plurality of individual protrusions spaced about the chimney 58. The first ring 302 of the flexible valve 300 surrounds the chimney 58 and rests against the stop 400 in a closed position. A first opening 310 in the first ring 302 rests against and/or is sealed by the The chimney 58 may also include a pronged portion 402 against which an inner base 447 of the first ring 302 rests in the closed position. A first opening 310 in the first ring 302 rests against and/or is sealed by the pronged portion 402 of the chimney 58 in the closed position. The second ring 304 also surrounds the chimney 58 and rests against the one or more protrusions 297 in the closed and open positions.

In at least one example embodiment, the flexible valve 300 may be made of a flexible and/or compressible material such as rubber or plastic. The material is resilient. The material is a food-grade material that does not react with the pre-vapor formulation.

Figure 17:
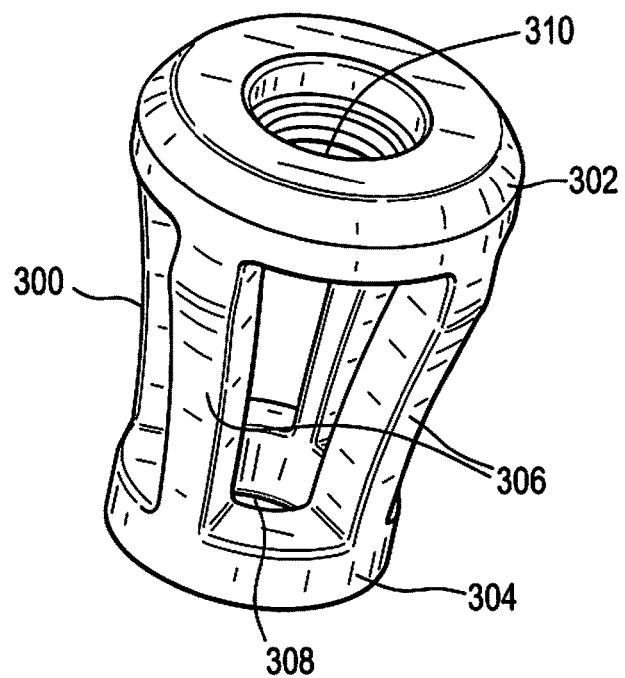
FIG. 17 is a perspective view of the valve of FIG. 16 according to at least one example embodiment.

FIG. 17 is a perspective view of the valve of FIG. 16 according to at least one example embodiment.

In at least one example embodiment, as shown in FIG. 17, the flexible valve 300 may include the first ring 302 connected to the second ring 308 by the one or more pillars 306. As shown, the first ring 302 has a larger diameter than the second ring 308, such that the first ring 302 has a diameter that is slightly less than an inner diameter of the housing 70. Thus, pre-vapor formulation may travel between the outer housing 70 and the first ring 302 when the flexible valve 300 is in an open position. The one or more pillars 306 may decline from the first ring 302 to the second ring 304, such that the one or more pillars 306 may be generally concave. The flexible valve 300 may also include a first opening 310 that seals against the pronged portion 402 in the chimney 58, and a second opening 308 through which the chimney 58 extends (as shown in FIG. 16).

Figure 18:
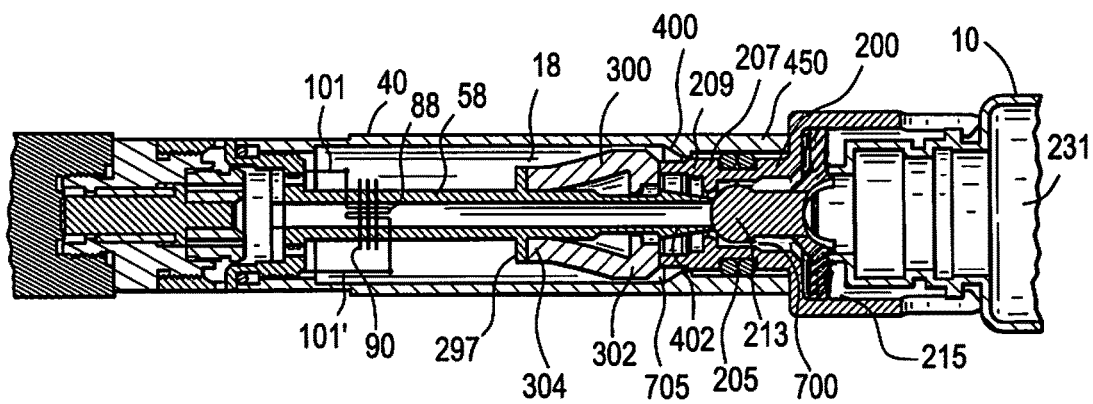
FIG. 18 of a cross-sectional view of the cartridge of FIG. 16 mated with the refill container of FIG. 14 according to at least one example embodiment.

FIG. 18 is a cross-sectional view of the cartridge 40 of FIG. 16 mated with the refill container of FIG. 14.

In at least one example embodiment, as shown in FIG. 18, when the neck 207 of the refill interface 200 is inserted into the neck 450 of the cartridge 40, the O-ring 205 seals the opening to prevent leakage of the pre-vapor formulation during filling. The chimney 58 presses against the flexible ball valve 213 in the neck 207, such that the flexible ball valve 213 seals the chimney 58, and the flexible ball valve 213 is pressed downwards within the refill interface 200. When the flexible ball valve 213 is pressed downwards, a space 700 is created between the flexible ball valve 213 and the neck 207 to allow pre-vapor formulation to flow from the reservoir 231, through the openings 217 in the flexible ball valve 213, through the neck 207, and into the reservoir being refilled. Simultaneously, the at least one protrusion 209 of the neck 207 presses against the first ring 302 of the flexible valve 300, so as to cause the flexible valve 300 to flex as the second ring 304 presses tightly against the one or more chimney protrusions 297. As the flexible valve 300 flexes, the pillars 306 bulge inwardly and the first ring 302 moves away from the stop 400 to create a space 705 through which the pre-vapor formulation flows into the reservoir 18.

Figure 19:
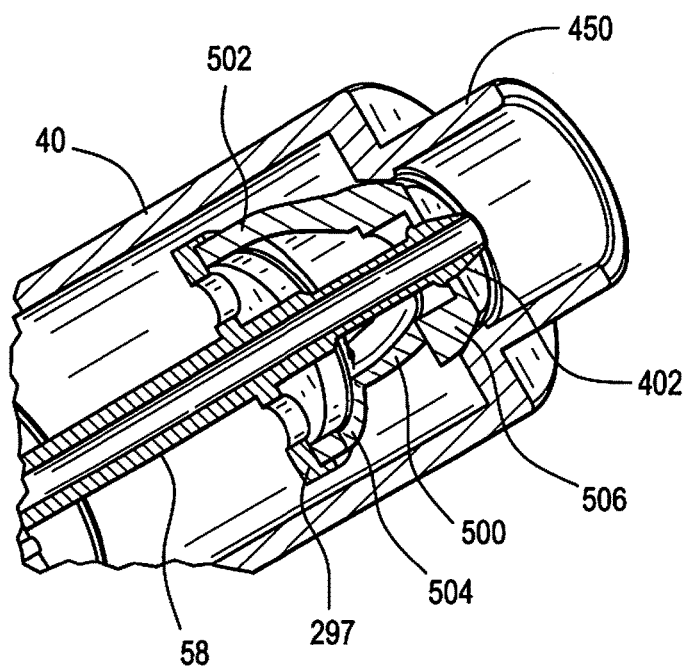
FIG. 19 is a cross-sectional, perspective view of a cartridge including a valve according to at least one example embodiment.

FIG. 19 is a cross-sectional, perspective view of a cartridge including a flexible valve according to at least one example embodiment.

In at least one example embodiment, as shown in FIG. 19, the cartridge 40 is generally the same as in FIG. 16, except that the flexible valve 500 includes one or more pillars 502 that extend outwardly from a first ring 506 to a second ring 504, such that the pillars 502 are generally convex in shape.

Figure 20:
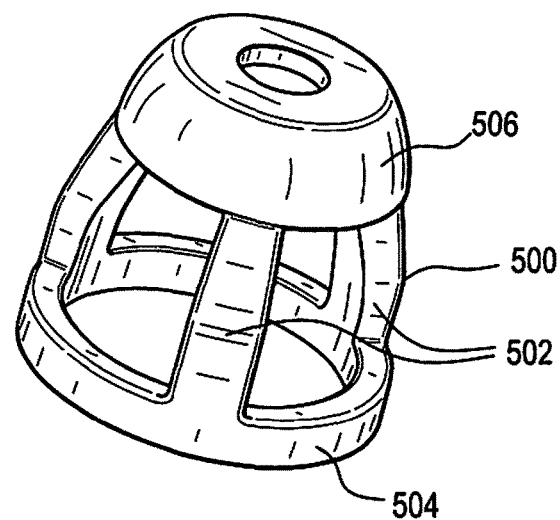
FIG. 20 is a perspective view of the valve of FIG. 19 according to at least one example embodiment.

FIG. 20 is a perspective view of the flexible valve of FIG. 19 according to at least one example embodiment.

In at least one example embodiment, as shown in FIG. 20, the flexible valve 500 may include three pillars 502 connecting the first ring 506 to the second ring 504. The pillars 502 may be substantially uniformly spaced about a circumference of each of the first ring 506 and the second ring 504.

Figure 21:
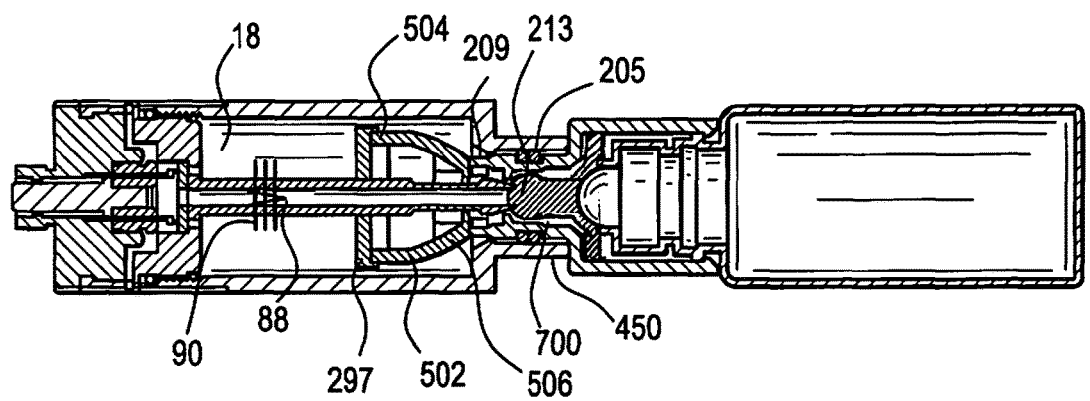
FIG. 21 is a cross-sectional view of the cartridge of FIG. 19 mated with the refill container of FIG. 14 according to at least one example embodiment.

FIG. 21 is a cross-sectional view of the cartridge 40 of FIG. 19 mated with the refill container of FIG. 14.

In at least one example embodiment, as shown in FIG. 21, when mated, the ball valve 213 presses against the chimney 58 and the protrusions 209 press against the first ring 506 causing the flexible valve 500 to flex and allow pre-vapor formulation to enter the reservoir 18.

In at least one example embodiment, as shown in FIG. 21, instead of a filamentary wick 90 and heater 88 as shown in FIG. 16, the heater 88 may be a planar, surface heater adjacent to and/or in contact with a wick 90 extending from a base of the reservoir 18. In another example embodiment, the filamentary wick 90 and/or heater 88 may be positioned at a base of the reservoir 18.

Figure 22:
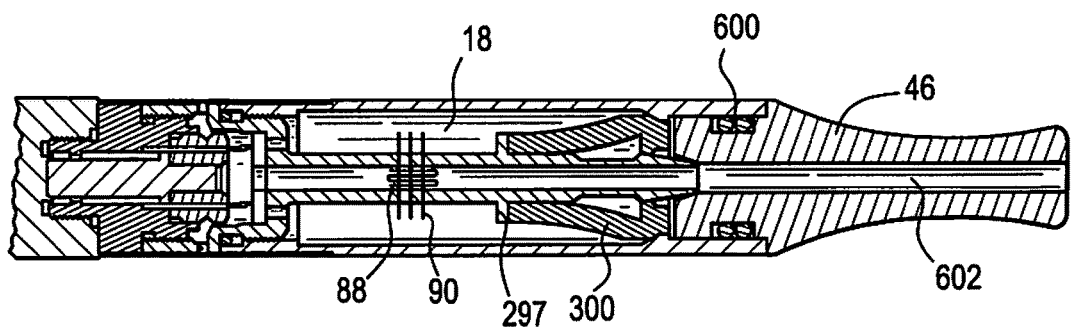
FIG. 22 is a perspective view of a cartridge including a mouthpiece according to at least one example embodiment.

FIG. 22 is a cross-sectional view of a cartridge 40 including the valve of FIG. 16 and including a removable mouthpiece 46.

In at least one example embodiment, as shown in FIG. 22, the mouthpiece 46 may include an outlet 602 extending though the mouthpiece 46. One or more O-rings 600 may circumscribe an outer portion of the mouthpiece 46 and may aid in reducing and/or preventing leakage of pre-vapor formulation from the reservoir 18.

Figure 23:
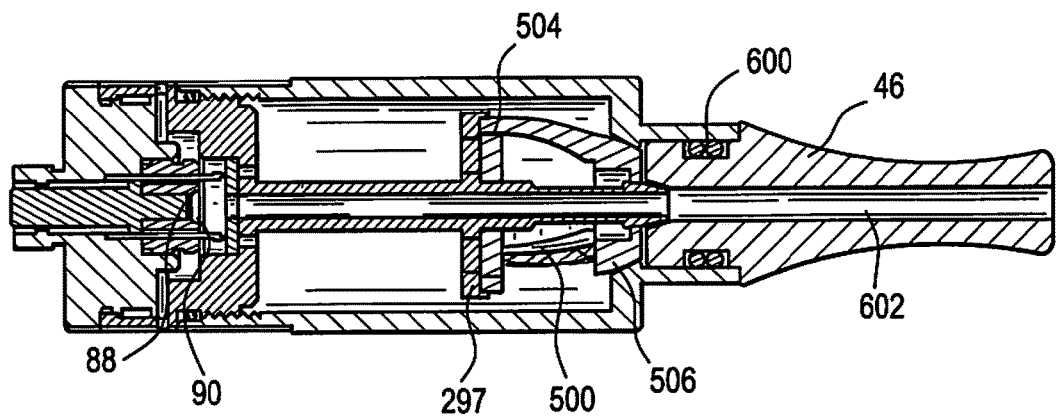
FIG. 23 is a perspective view of a cartridge including a mouthpiece according to at least one example embodiment.

FIG. 23 is a cross-sectional view of a cartridge 40 including the valve of FIG. 19 and including a removable mouthpiece 46.

In at least one example embodiment, as shown in FIG. 23, the cartridge 40 includes the flexible valve 500 of FIG. 19 and the mouthpiece 46 of FIG. 22.

When the word "about" is used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages. The expression "up to" includes amounts of zero to the expressed upper limit and all values therebetween. When ranges are specified, the range includes all values therebetween such as increments of 0.1%.

Moreover, when the words "generally" and "substantially" are used in connection with geometric shapes, it is intended that precision of the geometric shape is not required but that latitude for the shape is within the scope of the disclosure. When used with geometric terms, the words "generally" and "substantially" are intended to encompass not only features which meet the strict definitions but also features which fairly approximate the strict definitions.

It will now be apparent that a new, improved, and non-obvious electronic vaping device has been described in this specification with sufficient particularity as to be understood by one of ordinary skill in the art. Moreover, it will be apparent to those skilled in the art that numerous modifications, variations, substitutions, and equivalents exist for features of the electronic vaping device, which do not materially depart from the spirit and scope of the invention. For example, the refill bottle or tube may be any container configured to hold the pre-vapor formulation. Accordingly, it is expressly intended that all such modifications, variations, substitutions, and equivalents which fall within the spirit and scope of the invention as defined by the appended claims shall be embraced by the appended claims.

We claim:

1. A cartridge of an electronic vaping device, the cartridge comprising:
a reservoir configured to contain a pre-vapor formulation, the reservoir being refillable, and the reservoir including,
an opening, and
a first interlocking ring at the opening, the first interlocking ring including a plurality of grooves, a plurality of protrusions, or both a plurality of grooves and a plurality of protrusions spaced about a circumference of the first interlocking ring, the first interlocking ring configured to connect to a second interlocking ring attached to a refill container.

2. A cartridge of an electronic vaping device, the cartridge comprising:
a reservoir configured to contain a pre-vapor formulation, the reservoir being refillable, and the reservoir including,
an opening, the opening including,
a valve, the valve including a spring-loaded disk and a gasket, and
a first interlocking ring at the opening, the first interlocking ring including a groove, a protrusion, or both a groove and a protrusion, the first interlocking ring configured to connect to a second interlocking ring attached to a refill container.

3. The cartridge of claim 2, wherein the spring-loaded disk is configured to be depressed so as to allow pre-vapor formulation to flow into the reservoir.

4. The cartridge of claim 2, further comprising:
a chimney support configured to maintain the spring loaded disk in place until the first interlocking ring is connected to a second interlocking ring.

5. The cartridge of claim 2, further comprising:
a perforated disk including at least one perforation therein, the at least one perforation sized and configured to receive at least one tooth, the at least one tooth configured to depress the spring-loaded disk.

6. An electronic vaping device comprising:
a housing extending in a longitudinal direction;
a reservoir configured to contain a pre-vapor formulation, the reservoir in the housing, the reservoir being refillable, and the reservoir including,
an opening, and
a first interlocking ring at the opening, the first interlocking ring including a plurality of grooves, a plurality of protrusions, or both a plurality of grooves and a plurality of protrusions spaced about a circumference of the first interlocking ring, the first interlocking ring configured to connect to a second interlocking ring attached to a refill container;
a heater in fluid communication with the reservoir; and
a power supply configured to supply power to the heater.

7. An electronic vaping device comprising:
a housing extending in a longitudinal direction
a reservoir configured to contain a pre-vapor formulation, the reservoir in the housing, the reservoir being refillable, and the reservoir including,
an opening, the opening including,
a valve, the valve including a spring loaded disk, a perforated disk, and a gasket, and
a first interlocking ring at the opening, the first interlocking ring including a groove, a protrusion, or both a groove and a protrusion, the first interlocking ring configured to connect to a second interlocking ring attached to a refill container;
a heater in fluid communication with the reservoir; and
a power supply configured to supply power to the heater.

8. The electronic vaping device of claim 7, wherein the perforated disk includes at least one perforation therein, the at least one perforation sized and configured to receive at least one tooth, the at least one tooth configured to depress the spring-loaded disk so as to allow pre-vapor formulation to flow into the reservoir.

9. The electronic vaping device of claim 7, further comprising:
a chimney support configured to maintain the spring loaded disk in place until the first interlocking ring is connected to a second interlocking ring.

10. A reservoir refill system comprising:
a reservoir configured to contain a pre-vapor formulation, the reservoir including,
a reservoir body configured to contain the pre-vapor formulation,
an opening in the reservoir body, and
a first interlocking ring including a first groove, a first protrusion, or both a first groove and a first protrusion therein, the first interlocking ring positioned at the opening in the reservoir body; and
a refill container containing a pre-vapor formulation, the refill container including,
a container body,
an opening in the container body, and
a second interlocking ring including a second groove, a second protrusion, or both a second groove and a second protrusion therein positioned at the opening in the container body, the first interlocking ring configured to mate with the second interlocking ring, wherein the first groove, the second groove, of both the first groove and the second groove include a plurality of grooves, the first protrusion, the second protrusion, or both the first protrusion and the second protrusion includes a plurality of protrusions, the plurality of grooves and the plurality of protrusions are spaced about a circumference of the first interlocking ring, the second interlocking, or both the first interlocking ring and the second interlocking ring, and the plurality of grooves are sized and configured to mate with the plurality of protrusions.

11. The reservoir refill system of claim 10, wherein the first interlocking ring, the second interlocking ring, or both the first interlocking ring and the second interlocking ring are colored.

12. The reservoir refill system of claim 10, wherein the first interlocking ring and the second interlocking ring are the same color.

13. The reservoir refill system of claim 10, wherein the first interlocking ring, the second interlocking ring, or both the first interlocking ring and the second interlocking ring are formed of plastic.

14. The reservoir refill system of claim 10, wherein the opening in the reservoir further includes a valve.

15. The reservoir refill system of claim 14, wherein the valve includes a spring loaded disk, a perforated disk, and a gasket.

16. The reservoir refill system of claim 15, wherein the perforated disk includes at least one perforation therein, the at least one perforation sized and configured to receive at least one tooth, the at least one tooth configured to depress the spring-loaded disk so as to allow pre-vapor formulation to flow into the reservoir.

17. The reservoir refill system of claim 15, wherein the reservoir further comprises:

a chimney support configured to maintain the spring loaded disk in place until the first interlocking ring is connected to a second interlocking ring.

18. The reservoir refill system of claim 17, wherein the refill container further comprises:

a ball valve in a neck of the opening, the ball valve including a spring-loaded ball; and a crown adjacent the spring-loaded ball, the crown configured to shield the spring-loaded ball from being accessed.

19. The reservoir refill system of claim 10, wherein the first interlocking ring, the second interlocking ring, or both the first interlocking ring and the second interlocking ring are impregnated with a flavorant, a chemesthesis agent, or both the flavorant and the chemesthesis agent having a spicy taste, a bitter taste, a sour taste, a sub-combination thereof, or a combination thereof.

20. The reservoir refill system of claim 10, wherein the first interlocking ring, the second interlocking ring, or both the first interlocking ring and the second interlocking ring includes a coating comprising a flavorant, a chemesthesis agent, or both the flavorant and the chemesthesis agent having a spicy taste, a bitter taste, a sour taste, a sub-combination thereof, or a combination thereof.

21. The reservoir refill system of claim 10, further comprising:

a cap integrally formed with the first interlocking ring.

22. A method of refilling a reservoir of an electronic vaping device, the method comprising:

inserting at least one protrusion of a first interlocking ring into at least one groove of a second interlocking ring so as to engage a spring loaded ball of a refill container and a spring loaded disk of a reservoir; and releasing a formulation from the refill container to the reservoir.

* * * * *